United States Patent [19]

Bockow

[11] Patent Number: 5,650,157
[45] Date of Patent: Jul. 22, 1997

[54] PHARMACEUTICAL COMPOSITIONS AND METHODS

[76] Inventor: Barry I. Bockow, 16122 8th Ave. SW., Seattle, Wash. 98166

[21] Appl. No.: 247,682

[22] Filed: Mar. 22, 1994

Related U.S. Application Data

[63] Continuation of Ser. No. 53,508, Apr. 26, 1993, abandoned, which is a continuation of Ser. No. 816,833, Dec. 30, 1991, abandoned, which is a continuation of Ser. No. 545,414, Jun. 27, 1990, abandoned, which is a continuation-in-part of Ser. No. 520,026, May 7, 1990, abandoned.

[51] Int. Cl.$^6$ ...................................................... A61K 6/00
[52] U.S. Cl. ........................ 424/401; 424/523; 424/195.1
[58] Field of Search ................................. 424/401, 523, 424/195.1

[56] References Cited

U.S. PATENT DOCUMENTS

| | | | |
|---|---|---|---|
| 4,505,902 | 3/1985 | Millard | 424/195.1 |
| 4,710,383 | 12/1987 | Dick | 424/449 |
| 4,816,271 | 3/1989 | Scaffidi | 424/60 |
| 4,847,071 | 7/1989 | Bissett | 424/59 |
| 4,954,332 | 9/1990 | Bissett | 424/59 |

Primary Examiner—D. Gabrielle Phelan
Attorney, Agent, or Firm—Seed and Berry LLP

[57] ABSTRACT

Some otherwise desirable oil compositions derived from natural sources are characterized by an unpleasant odor. Fractions or combinations of such oils may also be so characterized. Stable, deodorized oils may be prepared by adding an amount of a deodorizing agent effective to substantially reduce the odor of the derived oil composition, fraction or combination thereof to that oil composition, fraction or combination. The pharmaceutical topical compositions of the present invention contain these stable, deodorized oil compositions and exhibit enhanced penetration properties and achieve enhanced patient response. The improved pharmaceutical compositions of the present invention may be used to manage pain and/or to treat the underlying ailments. Methods of making such topical pharmaceutical compositions are also discussed.

20 Claims, No Drawings

PHARMACEUTICAL COMPOSITIONS AND METHODS

CROSS-REFERENCE TO RELATED APPLICATIONS

This application is a continuation of U.S. Ser. No. 08/053,508, filed Apr. 26, 1993, now abandoned, which is a continuation of U.S. Ser. No. 08/816,833, filed Dec. 30, 1991, abandoned, which is a continuation of U.S. Ser. No. 07/545,414, filed Jun. 27, 1990, abandoned, which is a continuation in part of U.S. Ser. No. 07/520,026, filed May 7, 1990, now abandoned.

FIELD OF THE INVENTION

The present invention involves stable, deodorized oils and compositions containing such oils, wherein the oil component of the deodorized oil or the composition containing same has an unpleasant odor when standing alone without the benefit of conventional chemical processing for deodorization. The stable, deodorized oils of the present invention are prepared without conventional deodorization processing that adversely impacts oil stability and changes the chemical composition of the oil. More specifically, the present invention involves pharmaceutical compositions containing an active medicament and a stable, deodorized oil.

BACKGROUND OF THE INVENTION

Oils have many advantageous properties. Many cosmetic compositions contain fats and oils or materials derived from such fats and oils that serve as emollients and/or lubricants therein. Exemplary of such materials are triglyceride esters, fatty acids, fatty alcohols, soaps, detergents, cationic antiseptic and softener rinses, alkyl fatty acid esters, polyhydric alcohol esters, ethoxylated fatty alcohols, ethoxylated fatty ethers, ethoxylated sorbitan esters, branched-chain high-molecular weight alkyl esters, lanolin-derived fatty acids and fatty alcohols, other lanolin derivatives, and the like. In the pharmaceutical field, oils and fats are also used as emollients and/or lubricants in topical compositions, castor oil is useful as a cathartic, while chaulmoogra oil is used to treat Hansen's disease. Also, corn, sesame and cottonseed oils, for example, are employed as carriers for fat-soluble substances.

Marine animal oil compositions, in particular, have been suggested for a variety of uses as dietary supplements. For example, marine oil compositions are alleged to decrease cholesterol and triglycerides levels in humans, decrease prostaglandin synthesis, inhibit platelet aggregation and the like. Moreover, food processing concepts are being investigated to increase dietary intake of marine oils. Some proposals include incorporating fish oils into a wide variety of products, such as pastes and spreads, butter analogs and margarines, salad dressings, dairy foods, oils and oil blends, sausage, and smoked and spiced foods. Marine oil compositions or derivatives there of have also been used in both cosmetic and therapeutic topical formulations. For example, shark liver oil has been determined to be useful for the temporary protection of minor cuts, scrapes, burns and sunburn, and for the prevention and temporary protection of chafed, chapped or windburned skin and lips.

A non-fatty acid/ester component of marine oil compositions, often isolated, hydrogenated and included in topical compositions, is squalene, an unsaturated hydrocarbon $C_{30}H_{50}$. Squalene is also a component of adult human skin surface lipids. Squalene, itself, is not typically used in topical compositions due to its susceptibility to oxidation, resulting in formation of undesirable oxidation products. Primarily for this reason, squalene (hydrogenated squalene, also found in high concentrations in human skin surface lipids and obtained through chemical processing of squalene) is the hydrocarbon most often included in topical compositions.

While oral dosage forms containing oils, such as fish oils, have been developed and marketed as dietary supplements, the usefulness of topical preparations containing these oils has been limited by the unpleasant odor associated with such oils. When a composition is applied topically, any odor associated therewith becomes associated with the skin to which it is applied. As a result, consumer acceptability of topical compositions is highly influenced by the aroma thereof. Consequently, topical compositions having a malodorous oil component would not enjoy success in the marketplace.

The "off" or "rancid" odor associated with oils is produced, in part, by oxidation of polyunsaturated fatty acids contained therein. Since highly unsaturated fatty acids occur in greater proportion in marine animal oils than in common land animal and vegetable fats and oils, rancidity is a greater problem when using marine animal oils. Oxidation of polyunsaturated fatty acids leads to the formation of hydroperoxides. The decomposition products of these hydroperoxides, such as aldehydes resulting from oxidation of marine animal oils, exhibit the unpleasant odors characteristic of rancid oils. Certain decomposition intermediates have also been suggested to contribute to the unpleasant odor of some oxidized oils.

The "inherent" or "bland" odor of oils does not appear to arise from volatile components of oil compositions, which could be easily removed therefrom. Instead, these odors appear to be characteristic of the fatty acids or long-chain hydrocarbons associated therewith in natural oil compositions. In fish oils, for example, the "fishy" odor is postulated to be the result of interaction during oxidation between nitrogenous moieties and unsaturated glycerides present in the oil composition. Another theory regarding the source of the odor is that the unsaponifiable fraction (i.e., 5 hydrocarbon, sterol, methyl sterol, long-chain alcohol, triterpene alcohol, pigment, trace materials and the like) of the oil composition is the component with which the "fishy" odor is associated. In any event, this odor is not permanently removable even by drastic steam deodorization procedures (i.e., prolonged vacuum treatment at elevated temperatures, such as from about 230° to 260° C.). The odor returns upon exposure of the "deodorized" oil to oxygen.

Since marine oils are capable of imparting advantageous properties to topical compositions, efforts have been made to overcome the aroma problem. These efforts were complicated by the fact that many processes alter the composition of fats and fatty acids. Exemplary processing techniques are refining, high temperature clay bleaching, high temperature-high pressure fat splitting, distillation of fatty acids, molecular distillation of monoglycerides, transesterification reactions and partial hydrogenation. Alterations arising from processing include cis-trans isomerization, conjugation of polyunsaturates, polymerization, dehydration and the like.

Two strategies have emerged for using malodorous oils in topical compositions. In the first, only amounts of oil small enough not to adversely impact the odor of the complete topical composition were used. This strategy is not effective when higher concentrations of oil are required or desireable to impart advantageous properties to topical compositions.

Alternatively, to increase the percentage of oil which may be used within commercially acceptable topical compositions, chemical deodorization was explored. Barlow S. M. and Stansby M. E., eds., "Nutritional Evaluation of Long-Chain Fatty Acids in Fish Oil", page 20 Academic Press, London, 1982 describe a deodorization process featuring steam distillation conducted under a vacuum. The primary operating unit is a steel shell having trays disposed therein, maintained at from 2 to 5 mm Hg absolute pressure. The oil composition is heated to a process temperature of about 220° to 250° C. by steam, and volatiles, which adversely impact oxidative stability, are removed from the unit. Typical refining processes are also discussed in "Nutritional Evaluation of Long-Chain Fatty Acids in Fish Oil" at pages 13–20. Such refining processes include crude oil storage (to remove oil insolubles), degumming, neutralization, water washing, drying, bleaching, filtration, deodorization, polishing and the like.

Problems arose during the deodorization and refining processes, however, in that the processing steps changed the chemical composition of the oil itself (i.e., the composition being deodorized that resulted from minimal refining of the oil). For example, natural antioxidants, such as the various tocopherols which constitute vitamin E, were often either removed from the oil composition, broken down or chemically altered to such an extent that those antioxidants were functionally destroyed or impaired during deodorization or other oil processing. See, for example, *Bailey's Industrial Oil and Fat Products*, Volume 1, Fourth Ed., page 75, Daniel Swern, ed., John Wiley & Sons, New York, 1979. Caustic and steam oil refining processes remove at least a portion of tocopherol compounds from oil compositions. Carbon treatment of oil compositions also results in antioxidant removal. It has been determined that even small amounts of antioxidant may be sufficient to cause an increase in both resistance to oxidation and amount of oxidation required to produce rancidity. Primarily for this reason, natural fats containing antioxidants are much more resistant to oxidation than their pure triglyceride counterparts.

Since unsaturated fat and fatty acid components of an oil composition, such as triglycerides, diglycerides, alkoxydiglycerides (i.e., glycerol ethers), monoglycerides, omega-3 fatty acids, omega-9 fatty acids and the like, are susceptible to oxidation when exposed to air, the absence of these natural antioxidants from the oil composition leads to a decrease in the stability thereof. *Bailey's Industrial Oil and Fat Products* defines stability "as the resistance to autoxidation under prescribed conditions of aging . . . measured in units of time required for the product to (a) acquire a state of oxidation which can be correlated with organoleptic detection of rancid odor and flavor, or (b) to reach the end of the induction period if oxygen absorption measurement or peroxide analysis is used." The induction period is the time frame in which antioxidants effectively protect against oxidation. Once rapid oxidation sets in, antioxidants have little or no ability to curtail the reaction. Consequently, the presence of antioxidants in a composition constitutes a preventive measure rather than a corrective one.

Decomposition via oxidation can also cause a decrease in the percentage of unsaponifiable matter contained in an oil composition through oxidative degradation of hydrocarbons. Saponification is the reaction of a fatty acid, for example, with a base to produce a salt. Hydrocarbons, for example, cannot undergo such a reaction and are, thus, unsaponifiable. Exemplary unsaponifiable hydrocarbons found in oil compositions are squalene, gaducene, pristane, zamene, citorhenene and the like. The hydrocarbon squalene exhibits antioxidant activity under certain circumstances. Squalene also enhances percutaneous absorption of vitamin A and serves as a protective agent for human sebum. Other exemplary unsaponifiable components of fish oil are sterol, methyl sterol, long-chain alcohol, triterpene alcohol, pigment, trace materials, and the like.

Topical compositions are typically stored for some time prior to application thereof, and often are left standing open by users between such applications. Thus, stability of each component within a topical composition is considered in assessing the usefulness of the topical composition as a whole. A decrease in the stability of any component decreases the utility of the topical composition in which the component is dispersed. Moreover, antioxidants are not compound-specific protectants. That is, tocopherols dispersed in a topical composition would protect fatty acids, hydrocarbons and any other oxidation-susceptible component of that topical composition from oxidation. Thus, chemical deodorization of the oil composition can create stability problems for the topical product containing the oil composition by functionally impairing or destroying natural antioxidants.

Other, non-fatty acid components of an oil composition, such as vitamins, pro-vitamins (i.e., precursors of vitamins which are converted to vitamins in vivo), neovitamtns (i.e., isomeric forms of vitamins that function as vitamins in vivo), sterols, phosphatides, hydrocarbons and the like, may also be removed, functionally destroyed or functionally impaired during the deodorization or other oil processing. Alkali refining, for example, may significantly reduce the vitamin A content of oils, and carbon treatment of the oil composition may render the vitamin A component unstable. Hydrogenation processing may saturate vitamin A and decrease the biological activity thereof, unless precautions to preserve vitamin A activity are taken. Also, high temperature treatments, such as steam deodorization, decompose vitamin A provitamins.

These additional oil composition components, if intact, may also contribute other desirable properties to the topical composition as a whole. For example, vitamins, such as vitamin D and vitamin A, often significant components of oil compositions, serve certain biological functions. Vitamin E exhibits antioxidant properties as well as other vitamin E activity. Further, interrelation hips between the functions of vitamin A and vitamin E have been noted and attributed, in part, to the protective action of vitamin E with respect to vitamin A. Sterols, such as cholesterol, impart sterol activity in vivo. Phosphatides provide reinforcement to the action of other antioxidants.

It has now been recognized in the present invention that a substantially intact oil composition (i.e., a composition in which the components thereof are maintained in a form substantially equivalent to the natural form of those components) imparts advantageous properties to the ultimate topical composition containing the oil composition. The natural form of each of the components of the oil composition ingredient of the ultimate topical composition of the present invention is that form in which those components exist prior to refining. When chemical deodorizing processes are used, such components are modified and, as a result, chemical deodorization adversely impacts the ability of the oil component of the topical composition to impart advantageous properties to the ultimate topical composition.

Moreover, the natural form of the oil composition components typically includes one or more specific isomeric forms thereof. Other isomers may be created through oxidation, hydrogenation, partial hydrogenation, high temperature treatments and the like. For example, U.S. Pat. No. 4,843,095 indicates that saponification reactions converting triglyceride oil components to free fatty acids, if conducted under certain conditions, result in isomerization via cis-trans conversion. That is, the fatty acids resulting from the reaction do not correspond isometrically to the original triglyceride starting material. In addition, prior oil containing compositions were stabilized by hydrogenating the oil. It has now been discovered that hydrogenated fatty acids exhibit inferior penetration abilities in comparison with the natural polyunsaturated form of the fatty acids.

Estimates indicate that more than 35,000,000 U.S. adults and children suffer from pain. Some of these sufferers exhibit concomitant inflammatory conditions such as rheumatoid or psortatic arthritis. Other patients, however, do not fall into the inflammation category, but have a wide variety of musculoskeletal ailments including myofascial pain syndrome, tendoniris, bursitis, ligament attachment conditions or soft tissue complaints. An additional subset of patients exhibit chronic low-back pain that is not inflammatory but, nevertheless, requires pain management. Short-lived acute problems, such as tennis elbow, bursiris, and hip pointers, would also benefit from some form of pain management. Post trauma pain sufferers who have sustained ligamentous tears, miniscal tears, contusions, fractures or the like are another important patient subset. Metabolically-caused pain (i.e., gout, pseudogout, osteoporosis, primary underlying bone disease such as Paget's disease) requires management. In addition, treatment of patients with primary or secondary cancer are problematic for the clinician in view of these patient's pain management needs.

Almost all of the aforementioned patients suffering pain will be treated by physicians with nonsteroidal anti-inflammatory drugs, consisting primarily of chemical variations of ibuprofen. Regardless of the length of the half-lives of these routinely used drugs, administration thereof can result in serious undesirable side-effects. Estimates indicate that approximately 5% of the patients who receive these drugs will develop an NSAID-induced gastropathy that can lead to peptic ulceration, bleeding, hemorrhage, and even death. Moreover, patients in this 5% bracket are asymptomatic, and, as a result their first presentation to a hospital typically results from a GI hemorrhage. Other problems which may arise from the administration of anti-inflammatory drugs are compromised renal function, dermatological or cutaneous reactions, drug-induced hepatitis, enhanced salt retention, and, in rare cases, potentially fatal bone marrow depression. Patients with high blood pressure must be monitored carefully when being treated to manage pain, because the patient's hypertension may be augmented by the pain medication. Also, pain treatment available to children are severely limited as a result of the side-effects of these anti-inflammatory medications.

Given the problems incumbent in this entire class of medication, it is desirable to provide a therapeutic option allowing effective pain management with decreased risk of deleterious side-effects. It has been recognized by the present inventors that topical administration of anti-inflammatory agents may provide such an alternative. When administered directly to the afflicted area, high levels of the medicament may be directly delivered to produce a significant therapeutic response.

Thus, preparations containing oils or fractions or combinations thereof, which do not exude the unpleasant odor characteristic of such oils or oil fractions or combinations would be useful. In addition, since it has now been recognized that topical compositions containing oil compositions, with the components thereof maintained in their naturally occurring state stably therein (i.e., exhibiting no substantial chemical breakdown or alteration of those oil components) offer advantages over topical compositions containing conventionally processed oil compositions, maintenance of the components of an oil composition ingredient of a topical composition in a form substantially the same as its natural form during and after deodorization is desireable.

SUMMARY OF THE INVENTION

The present invention features pharmaceutical topical compositions containing a stable, deodorized oil, a fraction, or a combinations thereof and an active pharmaceutical ingredient. The active pharmaceutical component of the compositions of the present invention do not substantially adversely affect the structure and/or function of the oil component. Additional biologically acceptable adjuvants may be added to the topical compositions of the present invention. Preferred pharmaceutical components of the pharmaceutical topical compositions of the present invention are anti-inflammatory agents, analgesics, vasodilatory agents, anti-pruritic agents, anesthetics, protectants, counter irritants, astringents, antiseptics, keratolytic agents, anticholinergic agents, antihistamines, wound healing agents, and combinations thereof.

The stable, deodorized oils of the present invention, are capable of being used in topical compositions at high concentrations without imparting an unpleasant odor to such compositions. In accordance with the present invention, a stable, deodorized oil is a composition of matter including an oil composition characterized by an unpleasant odor or a fraction or combination of such oils so characterized and an amount of aloe effective to substantially deodorize the oil or fraction or combination thereof. A preferred embodiment of the oil useful in pharmaceutical compositions of the present invention is a stable, deodorized oil containing marine oils or omega-3 fatty acids. In addition to improved odor characteristics, the stable, deodorized oil of the present invention also exhibits enhanced skin-penetrating capability and imparts such enhanced capability to topical compositions containing the oil.

The pharmaceutical topical compositions of the present invention may be prepared by a process involving the steps of: admixing the malodorous oil composition or fraction or combination thereof with aloe; aging the mixture; and admixing the pharmaceutical ingredient and other adjuvants and the aged mixture. An alternative process for preparation of compositions in accordance with the present invention involves the steps of: admixing the malodorous oil composition or fraction or combination thereof, aloe, the pharmaceutical component, and other adjuvants; and aging the mixture.

DESCRIPTION OF PREFERRED EMBODIMENTS

As used in this specification, the term "oil composition" indicates a composition containing fats and/or fatty acids and other components derived from a natural oil source. Derivation may constitute minimal refining of the crude oil alone or include other processing, such as fractionation or combination of the oil composition. A synthetically prepared oil composition could be deodorized in accordance with the present invention, if necessary.

"Stable, deodorized oil composition", as used in this specification, is indicative of an oil composition in admixture with a deodorizing agent, such as aloe, capable of deodorizing the oil composition.

The term "topical composition", as used in this specification, indicates a composition containing a stable, deodorized oil composition in combination with a single or a plurality of topical adjuvants which do not interfere with the structure and/or function of the oil component.

An oil that may be stably deodorized in accordance with the present invention is any oil composition characterized by an unpleasant odor or a fraction or combination of oil compositions so characterized. In a preferred embodiment of the present invention, the oil composition is derived from a marine source. Exemplary sources of marine oils are fish, fish livers, shellfish, marine mammals and the like. Exemplary fish from which the preferred oils of the present invention may be derived are sharks, such as dogfish, bramble, Greenland, rough, saw, angel, bullhead, carpet, sand, tiger, thresher, basking, mackerel, cat, hound, weasel, requiem, hammerhead, sleeper and soupfin; cod, such as atlantic and pacific; herring, such as menhaden and anchovy; mackerel, such as common; haddock; halibut, such as pacific; perch, such as ocean; mullet, such as striped; pilchard; salmon, such as king, silver, sockeye, chinook, chum, coho and pink; sole, such as lemon; trout such as rainbow; tuna, such as bluefin, skipjack, albacore and yellowfin; whitefish, such as lake; pollock; ratfish; carp; flounder; hake; rockfish; sardines; whiting; sablefish; swordfish; and the like. Exemplary fish from which fish liver oil may be obtained are cod, such as atlantic; haddock; herring, such as pacific and atlantic; menhaden; pacific rockfish; pacific sablefish; pacific salmon, such as king, silver, chum, sockeye, pink; shark, such as dogfish, bramble, Greenland, rough, saw, angel, bullhead, carpet, sand, tiger, thresher, basking, mackerel, cat, hound, weasel, requiem, hammerhead, sleeper and soupfin; atlantic swordfish; tuna, such as albacore; saith; ling; dogfish; porbeagle; and the like. Exemplary shellfish from which oil compositions may be obtained are krill, clam, such as littleneck; crab, such as blue; oyster, such as pacific; scallop, such as sea; shrimp; lobster; and the like. Exemplary marine mammals are seals, whales and the like.

Marine oil compositions vary quite widely. As a result, the marine oil(s) used as a starting material in preparation of stable, deodorized oils or topical compositions of the present invention is selected based upon the desired characteristics of the resulting oil composition. An oil composition obtained from piked dogfish, for example, is suitable ingredient for cosmetic and therapeutic topical agents. Greenland sharks and ratfish oils, for example, have high glycerol ether content and little vitamin A, while oil obtained from cod livers contains vitamin D. Salmon oil exhibits high etcosopentaenoic and docosahexaenoic acid contents. As compositions of various marine oils are known, a practitioner would be able to select suitable marine oils to achieve a desired oil composition.

The stable, deodorized oil compositions of the present invention may be derived from crude marine oils. Crude marine oils are obtained by grinding marine animal body portions and treating the ground material to remove marine oils therefrom. The exact content of such crude oils vary in accordance with a variety of factors. Crude oils may contain insoluble, colloidal and soluble components. Exemplary insoluble components of crude oil are moisture, rust, dirt and proteins which are not dispersed within a colloidal suspension. Exemplary colloidal components are proteins, phosphatides and carbohydrates. Exemplary soluble components are pigments, oxidation products, trace metals, phosphatides which are not dispersed in colloidal suspensions, sulphurous and nitrogenous compounds, free fatty acids, mono-, di- and tri-glycerides and unsaponifiable matter.

The oil composition to be deodorized may be obtained from marine animals by minimal refining thereof, such as by steam refining as described in Fishery Leaflet 233 distributed by the Fish & Wildlife Service of the united States Department of the Interior. Steam refining involves: grinding of the fish body or fish body portions, such as the liver; introduction of live steam into tanks containing the ground fish under agitated conditions; and oil separation by gravity or, preferably, by three-phase or sludger centrifuge. Fishery Leaflet 233 and U.S. Pat. No. 1,833,061 describe the acid digestion process for minimally processing crude oil. Fish body parts are ground and treated with an acid to achieve a pH of approximately 1.5. Subsequently, a cooking step, typically an incubation period which may optionally take place in temperatures of up to approximately 70° C. to speed up the process, is accompanied by agitation. Such subsequent cooking and agitation are employed to enhance oil separation and/or reinforce the action of other separating substances. Minimal refining using the acid digestion method is augmented by the enzymatic action of natural enzymes contained in proteinaceous portions of marine animals. These natural enzymes promote hydrolysis of marine protein to facilitate the separation of marine oils therefrom.

A suitable method of minimal processing of marine animal product to obtain a marine animal oil to be deodorized in accordance with the present invention is as follows: obtain fresh raw marine animal product having an oil content of at least about 20%, although a marine animal product of lower oil content may also be processed in this manner; grind the raw product; add water, preferably warm water at approximately 25° C. to increase the activity of the enzymes, in a ratio of from about 1:1 to about 3:1 water to waste by weight; mix the water and ground marine animal product until the mixture is uniform; adjust the pH of the mixture (i.e., add an acid, such as phosphoric acid or the like thereto) to between about 2.0 and 3.5, with about 2.8 being especially preferred to avoid decomposition (high pH) and sterilization (low pH) of the slurry; mix gently to avoid emulsion formation; let mixture stand at room temperature for approximately 24 hours to allow the oil to separate; repeat the previous two steps two or three times; draw off oil that has risen to the top of the mixing vessel; remove any particles suspended in the oil by the use of gravity filtration and fine or ultra fine filter paper or by centrifuge; heat oil to approximately 75° C. to enhance the stability of the oil and permit the oil to cool gradually.

Oil compositions useful within the present invention may be further processed by fractionation, for example, to obtain oil fractions useful in the present invention. Exemplary fractions are glycerol ether, vitamin A, neovitamin A, omega-3 fatty acid, omega-9 fatty acid, hydrocarbon, restim, and the like. The glycerol ether fraction of an oil composition preferably contains glycerol ethers of omega-3 fatty acids. Fractionation can be accomplished via known techniques, such as that described by Malins in "Fatty Acids and Glycerol Ethers in Alkoxydiglycerides of Dogfish Liver Oil", reprinted from Chemistry and Industry, 1960, pp. 1359–1360.

Combinations of oil compositions or fractions thereof are also contemplated by the present invention. Exemplary of such combinations are pink salmon and piked dogfish, which yields an oil combination of higher stability than pink salmon alone; and greenland shark and ratfish, yielding an oil combination having high glycerol ether and low vitamin A contents. Such combinations may be obtained via known techniques, such as simple mixing.

The preferred oil compositions of the present invention are rich in omega-3 fatty acids. Omega-3 fatty acids are long-chain, polyunsaturated fatty acids. Exemplary omega-3 fatty acids useful in the present invention are eicosapentaenoic acid, docosahexaenoic acid, docosapentaenoic acid and linolenic acids of the omega-3 series and the like.

Oil compositions of the present invention may also contain vitamins, such as vitamins A, E, D and the like; pro-vitamins, such as beta-carotene, alpha-carotene, gamma-carotene and the like; neovitamins, such as neovitamin A; hydrocarbons, such as squalene, gaducene, pristane, zamene and citorhenene, and the like; other long-chain fatty acids, such as restim, alkoxydiglycerides, essential fatty acids, omega-9 fatty acids and the like; sterols; phosphatides and the like.

The oil composition, fraction or combination of the present invention is stably deodorized by admixture with an amount of a deodorizing agent sufficient to substantially reduce the characteristic odor of the oil. Exemplary of such deodorizing agents are aloe compositions and the like.

Aloe compositions useful in the practice of the present invention may be obtained from a variety of species of aloe plants, such as *Aloe scototrina, Aloe Perryi* Baker, *Aloe ferox, Aloe africana, Aloe spicata, Aloe perfoliata, Aloe Vera, Aloe vulgaris, Aloe barbadensis* and the like. Aloe vera, the preferred aloe useful in the present invention, may also be obtained from a variety of commercial sources. While aloe vera available from each manufacturer varies somewhat regarding a number of characteristics, such commercially available substances are useful in the compositions of the present invention. For example, aloe vera is commercially available in hydrophilic and lipophilic forms, and both of these forms may be used in accordance with the present invention. Moreover, commercially available aloe vera is often dispersed within a carrier, such as IPM (i.e., isopropyl myristate), IPP (i.e., isopropyl palmirate), and the like. Other commercial "carrier" forms of aloe compositions feature aloe stabilized in a water-soluble gel, such as Veragel® and in a highly concentrated powder form (i.e., Veragel® 200). Both Veragel® products are available from Dr. Madis Laboratories, Incorporated. Each of these "carrier/ aloe" compositions may also serve as the aloe constituent of stable, deodorized oil compositions of the present invention.

The aloe and oil starting materials are preferably combined in a ratio of from about 1:1 to about 50:1 by weight, aloe vera to the oil composition, fraction or combination thereof. Higher ratios would also function in accordance with the present invention. More preferably, the combination is in a ratio of from about 1:1 to about 15:1 by weight aloe vera to oil composition, fraction or combination thereof, with a ratio from about 1:1 to about 5:1 still more preferred. Guidelines for the use of commercially available aloe vera formulations follow. Aloe in combination with substances, such as IPM and IPP (i.e., aloe in a lipophilic carrier), gives best results when admixed with oil in an aloe:oil ratio of from about 1:1 to about 4:1, although higher ratios may be used in the practice of the present invention. Gels containing aloe dispersed therein (i.e., aloe in a hydrophilic carrier) are preferably admixed with oil in an aloe:oil ratio of from about 2:1 to about 6:1, although higher ratios may be used in the practice of the present invention. The aloe/oil mixture may be accomplished in any conventional manner sufficient to provide adequate admixture thereof.

Increased stability is provided to the deodorized oil of the present invention in comparison to that of prior art products. This enhanced stability is due, at least in part, to the nature of the deodorization process of the present invention. Merely admixing an aloe composition in one of its many forms does not result in undesired side reactions which modify the chemical structure and/or function of the components of the oil composition. Moreover, the conditions under which the mixing takes place are mild and do not disrupt the chemical structure and/or function of the components of the oil composition. As a result, natural antioxidants contained within the oil composition are not degraded and, consequently, the deodorized oil is less likely to undergo autoxidation upon exposure to air.

The stable, deodorized oil of the present invention also exhibits enhanced penetration capability in comparison to prior deodorized oil products. One reason for the enhanced penetration characteristics is that the deodorization process of the present invention permits the components of the oil composition to remain substantially intact (i.e., unchanged). In other words, the components of the oil composition are maintained in their natural form throughout the deodorization process. Orally delivered omega-3 fatty acids, for example, are known to be incorporated into cell membranes of platelets and endothelial cells. See, for example, Mueller and Talbert, *Clin. Pharm.*, 7(11): 795–807 (November 1988). Thus, the natural, substantially intact form of these fatty acids is recognized by the cells to such an extent that these fatty acids are incorporated into the cell structure. Other components of the compositions, such as phosphatides, vitamins and the like are also recognized by cells. This cellular recognition aids in the penetration of the deodorized oil into interior cells when applied to an exterior cellular surface, such as the skin.

In addition, mixture of aloe vera with the oil composition does not occur under conditions that are conducive to isomerization of omega-3 fatty acids or other oil components. Such isomers may be created via oxidation, hydrogenation, partial hydrogenation, high temperature processing and like reactions involving the oil composition. For example, U.S. Pat. No. 4,843,095 indicates that saponification reactions converting triglyceride oil components to free fatty acids, if conducted under certain conditions, result in isomerization by cis-trans conversion. Such isomers are not recognized by cells to the same extent as the natural isomeric form(s) of oil composition components. Also, prior oil compositions were stabilized by hydrogenation. Isomers created in this stabilization process are not recognized by the body to the extent that the substantially intact, polyunsaturated, natural form of the fatty acid is recognized. Consequently, oil compositions containing cis-trans, hydrogenated or other isomers of natural oil composition components would not exhibit the enhanced penetration characteristics of deodorized oils of the present invention. Furthermore, oxidation of polyunsaturated fatty acids can lead to the formation of epoxides. Such epoxides are harmful to biomolecules, particularly proteins and nucleic acids. Thus, oxidation of fatty acid oil components reduces the usefulness of such an oil as a component in topical compositions.

Finally, the deodorization process of the present invention permits the non-fatty acid components of oil compositions of the present invention to remain intact and functional. For example, substantially intact vitamins present in the compositions of the present invention, such as vitamin A, E, D and the like, function as previously described. Substantially intact pro-vitamins present in the compositions of the present invention, such as alpha-, beta- and gamma-carotene and the like, function as previously described. Neovitamins, such as provitamin A, phosphatides and sterols function as described above, when substantially intact and present in compositions of the present invention. Substantially intact hydrocarbons, such as squalene, gaducene, pristane, zamene and citorhenene and the like, function as described above, when dispersed in compositions of the present invention. Substantially intact non-omega-3 fatty acids, such as omega-9 fatty acids, essential fatty acids, restim, glycerol ethers (i.e., alkoxydiglycerides) and the like, function as previously described, when dispersed in compositions of the present invention. Loss of these functions due to conventional chemical deodorization processing decreases the usefulness of the resultant deodorized product.

Another aspect of the present invention features compositions containing stable, deodorized oils. For example, the stable, deodorized oils of the present invention may be administered in oral dosage forms, such as in liquid or in capsule form. Adjuvants known in the art for use in oral dosage forms may be admixed with the stable, deodorized oils of the present invention to produce oral dosage forms by a practitioner in the art.

Preferred compositions of the present invention are stable topical compositions having enhanced penetration properties. The topical compositions of the present invention include an oil composition, wherein the oil is characterized by an unpleasant odor, or a fraction of an oil so characterized or a combination of oils or fractions thereof so characterized; an amount of deodorizing agent effective to substantially reduce the odor of said oil, fraction or combination thereof; and at least one adjuvant suitable for topical use that does not adversely impact the structure and/or function of the oil, fraction or combination thereof. Preferably, oil compositions of the present invention include an omega-3 fatty acid component.

The enhanced penetration capability of topical compositions of the present invention appears to result, in part, form the maintenance of certain oil composition components in their natural states that are recognized by cells in vivo. This increase in cellular recognition enhances the penetration of a topical composition containing the recognized substances. Increases in oil content of the topical composition also contribute to the enhanced penetration capability of the topical compositions of the present invention.

As adjuvants useful in the present invention, standard adjuvants such as those utilized in cosmetic or pharmaceutical topical agents are contemplated, so long as the adjuvants are suitable for topical use and do not disrupt the structure and/or function of the oil composition. Exemplary adjuvants are thickeners, emulsifiers, humectants, antibacterials, emollients, ultraviolet absorbers, antibiotics, antioxidants, antihistamines, fungicides, disinfectants, dyes, pearlescents, keratolytic agents, absorbants, anti-caking agents and the like. For a more exhaustive list of typical adjuvants, see McCutcheon's 1982 *Functional Materials*.

Exemplary thickeners are water soluble thickening agents, such as gum arabic, karaya gum, gum tragacanth, guar gum, carob bean gum, tara gum, pectines, algtnates, carraghenates, agar, furcellaria, starches and the like; cellulose derivatives, such as methylcellulose, hydroxymethyl cellulose, hydroxyethyl cellulose, hydroxypropyl cellulose, hydroxypropylmethyl cellulose and the like; synthetic polymers, such as sodium polyacrylate, polyvinyl alcohol, carboxylic polymer derivatives of acrylic acid; and the like.

Emulsifiers used in topical compositions according to the present invention may be anionic, cationic or non-ionic. Exemplary anionic emulsifiers are alkali or alkaline earth soaps, such as sodium stearate, calcium oleate and the like; soaps of organic bases; sulfate or sulfone salts, such as sodium lauryl sulfate; and the like. Exemplary cationic emulsifiers are quaternary ammonium salts, such as benzalkonium chloride and cetyl pyridinium chloride, and the like. Exemplary non-ionic emulsifiers are aliphatic fatty alcohols, such as cetyl alcohol, stearyl alcohol and the like; fatty alcohols or alpha-diols, either oxyethylenated or polyglycerolated; cyclic fatty alcohols; glycol esters of fatty acids, such as ethylene glycol stearate, mono- or di-stearates of glycerol and the like; polyethyleneglycol esters of fatty acids, such as polyethylene glycol stearate and the like; esters of fatty acids of sorbitan; sucrose esters of fatty acids; and the like.

Additional ingredients, such as perfumes or other odor masking compounds may also be added to the compositions of the present invention. Fragrances, perfuming agents and other odor-masking compounds are known and readily available.

Since the oil compositions of the present invention exhibit enhanced penetrating abilities, the penetration of adjuvants and other composition components will also be enhanced. In cosmetic applications, cosmetic ingredients that exhibit beneficial properties will penetrate the outer dermal layers with greater efficiency and speed. This enhanced penetration will lead to improved absorption of desireable ingredients, such as hyaluronic acid, collagen, lanolin, cocoa butter, calendula oil, avocado oil, apricot kernel oil, vitamin E, herb extracts, yucca, jojoba oil and the like. In medicinal applications, enhanced absorption of efficacious molecules will be achieved. The medicinal benefit of enhanced penetration of a topical agent can be garnered in treatment of both animals and humans.

A typical adjuvant formulation suitable for topical application in accordance with the present invention is 3.0% (% by weight of total composition) glycerol monostearate; 2.0% cetyl alcohol; 3.5% stearic acid; 0.10% propyl paraben; 1.0% jojoba oil; 2.0% isopropyl palmirate; 1.0% triethanolamine; 4.0% propylene glycol; 0.15% methyl paraben and 80.0% water.

Due to the level and duration of deodorization attainable in accordance with the present invention, the oil composition component may constitute a high percentage by weight of the total topical compositions. When the present invention is practiced, the economic attractiveness of using water as a component of a topical composition replaces oil composition odor as the limiting factor with respect to the percentage of oil in that topical composition. Preferably, topical compositions of the present invention contain at least 2–3% by weight oil composition component with at least 10% Oil more preferred. Practically, an upward limit on the percentage of oil composition within the topical compositions of the present invention is approximately 50%. However, topical compositions containing higher percentages can be prepared.

The topical compositions of the present invention may be prepared in accordance with the following procedure: admixing the oil composition, fraction or combination thereof with aloe; aging the mixture; and admixing topical adjuvants with the aged mixture. Alternatively, topical compositions in accordance with the present invention may be prepared by the following method: admixing the oil composition, fraction or combination thereof, aloe and topical adjuvants; and aging the mixture. Mixing steps in both methods may be accomplished under appropriate mild conditions and in accordance with known techniques.

Aging the oil:aloe mixture or the topical composition as a whole may allow interactions between components to take place slowly in the absence of the application of high temperatures or other harsh reaction conditions. The choice of the best preparation methodology for use with a specific formulation is dependent upon the nature of the aloe used. If the aloe is lipophilic, the oil:aloe mixture is preferably aged prior to mixture with the topical adjuvant(s). Otherwise, the complete topical composition is aged. In either event, the duration of the aging process is the same, i.e., from about 3 to about 14 days, with from about 6 to about 10 days preferred. The deodorization proceeds gradually during the aging process which is preferably carried out under anaerobic conditions.

Optionally included within the topical compositions of the present invention are pharmaceutically active agents capable of dispersion within the topical composition and which impart pharmaceutical benefit to the area of the body to which the agent is applied or to an area physically or systemically interrelated therewith. That is, if the topical composition is applied to a specific skin area, the pharmaceutically active ingredient must either act on the skin itself, penetrate the skin to act on deep soft tissues, joints, bursers, ligaments, tendons, muscles, and the like, or penetrate into the bloodstream to be carried to the afflicted area.

Exemplary pharmaceutically active agents are those that are capable of imparting anti-inflammatory, analgesic, vasodilatory, anti-pruritic, anesthetic, protectant, counterirritant, astringent, antiseptic, keratolytic, anticholinergic, antihistamine, wound healing and like pharmaceutical benefits to an afflicted area. Methyl salicylate, benzocaine, dibucaine, phenylephrine hydrochloride, zinc oxment kaolin, calamine, camphor, menthol, salicylic acid, coal tar, allantoin, live yeast cell derivatives, boric acid, phenol, resorcinol, precipitated sulfur, afropine, juniper tar, hydrocortisone and the like are exemplary pharmaceutically active agents useful in accordance with the present invention.

Exemplary ailments which may be treated using a topical composition of the present invention in admixture with a pharmaceutically active agent are bursiris, tendonitis, epicondylitis, myofacial pain syndrome, myositis, degenerative and inflammatory arthritis, vasospastic disorders, neck pain, lower back pain, sciatica, post exercise pain, post operative swelling, burns, diaper rash, itching, acne, sunburn, windburn, fever blister, cold sore, insect bite, insect sting, poison ivy, poison oak, poison sumac, anorectal disorders, dermatitis, such as seborrheic dermatitis, psoriasis, fungus, other skin conditions, such as some types of skin discoloration, ophthalmic disorders, and the like. A topical composition of the present invention may also be used as a carrier for sunscreening agent, such as para-aminobenzoic acid, octyl dimethyl para-aminobenzoic acid, cinoxate, homosalate, octyl methoxycinnamate and the like and, additionally, as a carrier for agents screening against precancerous and/or cancerous-inducing lesions and the like.

Local anesthetics, for example, may be included is pharmaceutical compositions formulated for the treatment of burns, insect bites or stings, sunburn, and the like. Exemplary local anesthetics are benzocaine, dibucaine, benzyl alcohol, dibucaine hydrochloride, lidocaine, pramoxine hydrochloride, tetracaine, and tetracaine hydrochloride.

Analgesic, anesthetic and antipuritic compounds may also be included within pharmaceutical compositions. Exemplary of such compounds are juniper tar, camphor, menthol, and methyl salicylate. At higher concentrations, these compounds act as counterirritants and increase circulation.

Topical compositions for the treatment of conditions, such as seborrheic dermatitis, psoriasis, and the like, may also be formulated in accordance with the present invention. Such compositions would include pyrithione zinc, salicylic acid, selenium sulfide, sulfadiazine, sulfur, or a combination thereof.

An exemplary antibiotic cream of the present invention includes a neomycin sulfate active ingredient. Exemplary anti-ache compositions of the present invention contain sulfur or zinc oxide active agents. An exemplary anti-inflammatory, anti-inch composition of the present invention includes a hydrocortisone acetate active ingredient. Also, an exemplary liniment composition of the present invention includes at least one active agent selected from menthol, camphor, and eucalyptol.

The amount of a specific active pharmaceutical ingredient or ingredients included within a pharmaceutical topical composition of the present invention is dependent upon a variety of factors, such as the miscibility of the pharmaceutical, the stabilized oil, and the adjuvants, the typical effective dose of the pharmaceutical, and the like. Generally, the amount of a pharmaceutical ingredient included within a topical composition will range from about 0.1% to 5% by weight of that composition, with from about 2% to about 20% being preferred. For methyl salicylate, for example, the topical composition will include from about 5% to 20% by weight of the pharmaceutical, with from about 10% to about 15% being preferred.

The present invention also contemplates general topical skin protectant compositions. A skin protectant is defined by the Food and Drug Administration as "[a]drug which protects injured or exposed skin or mucous membrane surface from harmful or annoying stimuli." Exemplary skin protectants and approximate active percentages follow:

allantoin (from about 0.5% to about 2.0% by weight).

aluminum hydroxide gel (from about 0.15% to about 5.0% by weight).

calamine (from about 1.0% to about 254 by weight).

cocoa butter (from about 50% to 100% by weight).

dimethicone (from about 1.0% to about 30% by weight).

kaolin (from about 4.0% to about 20% by weight).

zinc acetate (from about 0.1% to about 2.0% by weight).

zinc carbonate (from about 0.2% to about 2.0% by weight).

zinc oxide (from about 1.0% to about 25% by weight).

For a protectant for use with minor cuts, scrapes, and burns including sunburn, allantoin and/or cocoa butter are exemplary preferred active ingredients. For prevention and treatment of chafed, chopped, cracked or windburned skin and lips, exemplary preferred active ingredients are allantoin and/or cocoa butter and/or dimethicone. To dry poison ivy, poison oak, and poison sumac, compositions containing one or more exemplary preferred active ingredients, such as aluminum hydroxide gel, calamine, kaolin, zinc acetate, zinc carbonate, and zinc oxide.

The amount of the pharmaceutical topical composition applied and the number of applications thereof is dependent on a number of factors. Primarily, the treatment will be dictated by the patient's condition and therapeutic response to the treatment. A clinician would be able to ascertain an appropriate treatment protocol. Typically, the topical composition will be administered twice daily for 7 to 10 days; however, more or less frequent administration and/or shorter or longer treatment duration may be employed in accordance with sound medical practices.

Moisturizer Formulation. To form a moisturizing composition in accordance with the present invention, three compositions, designated A, B and C are formed as follows:

| Composition | Ingredient | % By Weight Total Composition |
|---|---|---|
| A | Shark Liver Oil | 3.0 |
|   | Jojoba oil | 1.0 |
|   | Isopropyl Palmitate | 2.0 |
|   | Cetyl Alcohol | 2.0 |
|   | Stearic Acid XXX* | 3.5 |
|   | Glycerol Monostearate | 3.0 |
|   | Propyl Paraben | 0.10 |
| B | Triethanolamine | 1.0 |
|   | Aloe Veragel ® 200** | 0.25 |
|   | Propylene Glycol | 4.0 |
|   | Methyl Paraben | 0.15 |
|   | Water | 80.0 |
| C | Fragrance | q.s. |

*Triple pressed stearic acid.
**Aloe concentrated 200 times available from Dr. Madis Laboratories, Incorporated.
q.s. = quantity sufficient.

Composition A is heated at 80° C. and admixed until uniform.

Composition B is heated at 80° C. and admixed until a solution is formed. Composition B is slowly added to composition A under agitated conditions. Agitation is continued at a slow rate and the combined composition is allowed to cool to 45° C. Composition C is added and agitation is continued while the composition is allowed to cool to 30° C. The mixture is aged at 20° C. for 10 days, resulting in a composition with an acceptable odor for topical applications.

Analgesic Cream. To form an analgesic composition in accordance with the present invention, four compositions, designated A, B, C and D are formed as follows:

| Composition | Ingredient | % By Weight Total Composition |
|---|---|---|
| A | Cod Liver | 5.0 |
|   | Veragel ® Lipoid 1:1* | 5.0 |
| B | Glycerol Monostearate | 3.0 |
|   | Cetyl Alcohol | 2.35 |
|   | Stearic Acid XXX | 4.0 |
|   | Propyl Paraben | 0.10 |
| C | Menthol | 0.10 |
|   | Camphor | 0.20 |
|   | Oil of Eucalyptus | 0.10 |
| D | Triethanolamine | 1.0 |
|   | Propylene Glycol | 3.0 |
|   | Methyl Paraben | 0.15 |
|   | Water | 76.0 |

*From Dr. Madis Laboratories, Incorporated.

The ingredients in composition A are admixed and permitted to age at 20° C. for 4 days to produce a composition with an odor acceptable for topical applications. Composition D is heated to 60° C. Composition B is added to D slowly, and the admixed compositions are agitated until the resultant composition is uniform. Composition A is slowly added to the combined D/B composition, and agitation is continued while the D/B/A mixture is cooled to 45° C. Composition C is added, and the composition is agitated while being cooled to 30° C.

Burn Cream. To form a burn treatment composition in accordance with the present invention, three compositions, designated A, B and C are formed as follows:

| Composition | Ingredient | % By Weight Total Composition |
|---|---|---|
| A | Fish Oil Fraction | 10.0 |
|   | Aloe Vera Gel* | 45.0 |
| B | Isopropyl Myristate | 2.0 |
|   | Cetyl Alcohol | 2.5 |
|   | Glycerol Monostearate | 3.0 |
|   | Benzocaine | 2.05 |
|   | Propyl Paraben | 0.10 |
| C | Triethanolamine | 1.0 |
|   | Propylene Glycol | 4.0 |
|   | Allantoin | 0.2 |
|   | Water | 30.0 |
|   | Methyl Paraben | 0.15 |

*From Golden Horizons International, Limited.

The ingredients of composition A are mixed until uniform, and aged for 5 days, resulting in a composition with an odor acceptable for topical applications. Composition C is heated to 80° C. Composition B is added to composition C slowly and the B/C mixture is cooled to 45° C. under agitation. Composition A is added to the cooled B/C mixture and agitation is continued until the topical composition has cooled to 30° C.

Cosmetic Application Protocol. A moisturizing cream prepared in accordance with the procedure described above may be applied to the skin of a user having dry skin twice daily to enhance the vitality of the skin to which the cream is applied.

Therapeutic Protocol A. An analgesic composition prepared in accordance with the procedure described above may be administered by topical application to the injured area of a patient suffering from a sports-related tendon injury twice a day for ten days or less. Pain relief is expected to be observed.

Therapeutic Protocol B. An analgesic composition prepared in accordance with the procedure described above may be administered by topical application to the injured area of a patient suffering from a rheumatoid arthritis twice a day for ten days or less. Pain relief is expected to be observed.

Therapeutic Protocol C. A burn cream prepared in accordance with the procedure described above may be administered by topical application to the burn of a patient suffering from a third degree burn twice a day for ten days or less. Pain relief is expected to be observed.

Patient Trial Results

Analgesic pharmaceutical formulations containing shark oil and aloe vera within the percentages set forth above and approximately 10% by weight methyl salicylate were prepared substantially in accordance with the procedure described above. The pharmaceutical formulations were administered twice daily to patients suffering from a variety of medical problems. Table I indicates the patient's global assessment of their response to the topical composition (4=excellent; 3=Good; 2=Fair; 1=None).

TABLE I

| Patient ID | Diagnosis | Response |
|---|---|---|
| BJ | RA | 3 |
| DW | F, TE, B | 3 |
| JM | RA, F | 4 |

TABLE I-continued

| Patient ID | Diagnosis | Response |
|---|---|---|
| EB | F, TE, B | 4 |
| BG | F, B | 4 |
| NW | RA, B | 3 |
| EM | F, TE, B | 3 |
| AM | OA, F, B | 3 |
| SS | F, TE | 3 |
| CB | F, S, B | 3 |
| NR | F, TE | 3 |
| AD | OA | 4 |
| TO | B | 3 |
| GP | OA, F | 3 |
| PF | F | 3 |
| MP | OA, F | 3 |
| DC | F, TE, B | 3 |
| AT | OA, F | 3 |
| GM | OA | 4 |
| JM | F, B, TE | 4 |
| VS | B | 3 |
| GA | RA, B | 3 |
| DR | F, TE | 4 |
| FH | RA | 3 |
| LL | RA | 4 |
| JC | RA, B | 3 |
| GF | RA, F | 3 |
| EL | RA | 3 |
| KG | F, TE | 4 |
| JW | F | 2 |
| FK | OA, F | 4 |
| BR | RA | 2 |
| NB | F, TE | 2 |
| HK | OA, B | 3 |
| BP | TE | 4 |
| SK | PA | 4 |
| EM | TE, B | 3 |
| LL | F | 3 |
| PF | F | 4 |
| EA | F, OA | 4 |
| GD | OA | 3 |
| LG | RA | 4 |
| JA | OA | 2 |
| CE | RA, F | 3 |
| JR | F | 4 |
| CF | F, B, TE | 3 |
| MS | OA | 3 |
| DD | TE, B | 3 |
| SB | B, F | 4 |
| KG | F, B | 4 |
| BG | F | 3 |
| IS | F, RA | 4 |
| LU | F, OA | 3 |
| EF | B | 3 |
| MZ | F | 2 |
| GB | F | 3 |
| KR | B, RA | 2 |
| EF | F, RA | 3 |
| AL | B, TE | 0 |
| LJ | F, B | 4 |
| VQ | B | 0 |
| JR | F | 2 |
| CG | B | 4 |
| BH | B | 3 |
| AB | F | 3 |
| JB | OA | 4 |
| PA | OA | 4 |
| SS | OA | 3 |
| VH | F | 4 |
| BC | OA, F | 3 |
| JB | OA | 4 |
| PA | OA | 4 |
| CR | OA, F | 4 |
| GR | OA, F | 4 |
| MS | F | 4 |
| RE | F | 3 |
| AO | F | 3 |
| GP | RA | 4 |
| AK | RA | 4 |
| LK | OA | 4 |
| GL | F, B | 3 |
| CF | F | 0 |
| BF | OA | 4 |
| MP | F | 2 |
| KK | OA | 2 |
| FC | OA | 3 |
| DH | B | 3 |
| JA | OA, F | 3 |
| LH | B | 4 |
| GW | F, B, OA | 4 |
| GH | F, OA | 1 |
| RE | F | 3 |
| DM | F, B | 3 |
| HH | T | 3 |

(OA = Osteoarthritis; RA = Rheumatoid Arthritis; F = Fibrositis, Fibromyalgia, Musculoskeletal Pain, and Soft Tissue Rheumatism; B = Bursitis; TE = Tennis Elbow; S = Sjogren's Syndrome; PA = Psoriatic Arthritis)

The results indicate that 86% of the patients treated with the topical medicament exhibited good to excellent therapeutic responses.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A topical pharmaceutical preparation comprising a marine oil rich in omega-3 fatty acid, a deodorizing agent, and an effective amount of a pharmaceutically active ingredient, wherein the omega-3 fatty acid is at least 2% by weight of the preparation, and wherein the pharmaceutically active ingredient is selected from anti-inflammatory agents, analgesics, vasodilatory agents, anti-pruritic agents, anesthetics, counterirritants, astringents, antiseptics, keratolytic agents, anticholinergic agents, antihistamines, wound healing agents, and combinations thereof.

2. The topical pharmaceutical preparation of claim 1 wherein the omega-3 fatty acid is at least 3% by weight of the preparation.

3. The topical pharmaceutical preparation of claim 1 wherein the omega-3 fatty acid is at least 10% by weight of the preparation.

4. The topical pharmaceutical preparation of claim 1 wherein the omega-3 fatty acid is present in mono-, di- or tri-glyceride form.

5. The topical pharmaceutical preparation of claim 1 wherein the pharmaceutically active ingredient is selected from an anti-inflammatory agent, an analgesic, and a combination thereof.

6. The topical pharmaceutical preparation of claim 1 wherein the pharmaceutically active ingredient is salicylic acid.

7. The topical pharmaceutical preparation of claim 1 wherein the pharmaceutically active ingredient is methyl salicylate.

8. The topical pharmaceutical preparation of claim 1 wherein the pharmaceutically active ingredient is benzocaine.

9. The topical pharmaceutical preparation of claim 1 wherein the pharmaceutically active ingredient is an anti-inflammatory agent.

10. The topical pharmaceutical preparation of claim 1 wherein the pharmaceutically active ingredient is an analgesic.

11. The topical pharmaceutical preparation of claim 1 wherein the pharmaceutically active ingredient is a vasodilatory agent.

12. The topical pharmaceutical preparation of claim 1 wherein the pharmaceutically active ingredient is an antipruritic agent.

13. The topical pharmaceutical preparation of claim 1 wherein the pharmaceutically active ingredient is an anesthetic.

14. The topical pharmaceutical preparation of claim 1 wherein the pharmaceutically active ingredient is a counterirritant.

15. The topical pharmaceutical preparation of claim 1 wherein the pharmaceutically active ingredient is an astringent.

16. The topical pharmaceutical preparation of claim 1 wherein the pharmaceutically active ingredient is an antiseptic.

17. The topical pharmaceutical preparation of claim 1 wherein the pharmaceutically active ingredient is a keratolytic agent.

18. The topical pharmaceutical preparation of claim 1 wherein the pharmaceutically active ingredient is an anticholinergic agent.

19. The topical pharmaceutical preparation of claim 1 wherein the pharmaceutically active ingredient is an antihistamine.

20. The topical pharmaceutical preparation of claim 1 wherein the pharmaceutically active ingredient is a wound healing agent.

* * * * *